United States Patent
Lannigan et al.

(10) Patent No.: US 6,399,302 B1
(45) Date of Patent: Jun. 4, 2002

(54) SIGNAL GENERATING OLIGONUCLEOTIDE-BASED BIOSENSOR

(75) Inventors: Deborah A. Lannigan; Ian G. Macara, both of Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 0 days.

(21) Appl. No.: 09/529,870

(22) PCT Filed: Aug. 20, 1999

(86) PCT No.: PCT/US99/18904
§ 371 (c)(1),
(2), (4) Date: Apr. 19, 2000

(87) PCT Pub. No.: WO00/11446
PCT Pub. Date: Mar. 2, 2000

Related U.S. Application Data

(60) Provisional application No. 60/097,478, filed on Aug. 21, 1998.

(51) Int. Cl.[7] ............................. C12Q 1/68; C12M 1/34; C07H 21/04; C07H 21/02
(52) U.S. Cl. .................... 435/6; 435/287.1; 435/287.2; 435/288.3; 435/288.4; 435/288.7; 536/24.3
(58) Field of Search ..................... 435/6, 287.1, 287.2, 435/288.3, 288.4, 288.7; 536/23.1, 24.3

(56) References Cited

U.S. PATENT DOCUMENTS

| | | | |
|---|---|---|---|
| 4,536,479 A | * | 8/1985 | Vander-Mallie ............. 436/537 |
| 5,591,578 A | * | 1/1997 | Meade et al. .................. 435/6 |
| 5,637,459 A | * | 6/1997 | Burke et al. .................... 435/6 |
| 5,691,145 A | | 11/1997 | Pitner et al. |
| 5,763,599 A | | 6/1998 | Pfleiderer et al. |
| 5,843,653 A | * | 12/1998 | Gold et al. ..................... 435/6 |
| 5,925,517 A | * | 7/1999 | Tyagi et al. .................... 435/6 |
| 5,989,823 A | * | 11/1999 | Jaysena et al. ................ 435/6 |
| 6,027,880 A | * | 2/2000 | Cronin et al. .................. 435/6 |
| 6,242,246 B1 | * | 6/2001 | Gold et al. ............. 435/287.1 |

OTHER PUBLICATIONS

Lin, et al., "Inhibition of Multiple Thermostable DNA Polymerases by a Heterodimeric Aptamer," Journal of Molecular Biology, Academic Press Limited, vol. 271 (No. 1), p. 100–111, (Jun. 1997).

Ringquist, et al., "Anti–L–Selectin Oligonucleotide Ligands Recognize CD62L–Positive Leukocytes: Binding Affinity and Specificity of Univalent and Bivalent Ligands," Cytometry, Wiley–Liss, Inc., p. 394–405, (Dec. 1, 1998).

Ota, et al., "Determination of Interactions Between Structured Nucleic Acids by Fluorescence Resonance Energy Transfer (FRET): Selection of Target Sites for Functional Nucleic Acids," Nucleic Acids Research, Oxford University Press, vol. 26 (No. 3), p. 735–743, (1998).

Potyrailo et al. Anal. Chem. 70:3419–3425, Aug. 1998.*

* cited by examiner

Primary Examiner—Stephanie W. Zitomer
(74) Attorney, Agent, or Firm—John P. Breen

(57) ABSTRACT

The present invention relates to oligonucleotide-based biosensors and a general method for their production and use. Specifically, the invention describes a novel signal-generating ligand complex comprising the combination of two or more aptamers linked together by a polymeric linker and further comprising a signaling system that provides a detectable signal upon binding of the signal-generating ligand complex to its target analyte.

15 Claims, No Drawings

SIGNAL GENERATING OLIGONUCLEOTIDE-BASED BIOSENSOR

CLAIM TO PRIORITY

This application claims priority under 35 USC §119(e) to U.S. Provisional Application Serial No. 60/097,478, filed Aug. 21, 1998, the disclosure of which is expressly incorporated herein.

GOVERNMENTAL RIGHTS

This invention was made with government support under grant number 5-24320, awarded by the National Institutes of Health. The government has certain rights in the invention.

FIELD OF THE INVENTION

The present invention is directed to a new class of signal generating high-affinity nucleic acid ligands that specifically bind a desired target molecule and produce a detectable signal upon binding to the target molecule. A method is described for creating these signal-generating ligands, and for their use in assay methods, diagnostic procedures, cell sorting, and for other analytical procedures including their use as probes.

BACKGROUND OF THE INVENTION

The current methods of detecting specific analytes in complex mixtures (for example detecting complex organic compounds such as pesticides in a given sample) requires the extraction of the sample into organic solvents, followed by analysis using gas-liquid chromatography and/or mass spectroscopy. These methods are slow (several days, typically) and expensive ($100–$300 per single analysis, from a survey of commercial laboratories that perform these assays, in mid-1999). The development of a biosensor device that could detect/screen for a dozen or more different analytes within minutes would therefore provide a significant cost and time benefit.

Despite the widespread interest in the development of biosensors, little progress has been made, except on a case-by-case basis for single targets. One problem has been the lack of a general method for developing specific receptors for diverse types of targets. Several approaches to resolve this problem have been developed (see Turk, C, gold, L Science 249: 505–510 (1990); U.S. Pat. Nos. 5,843,653, and 5,843,701). The other, more intractable problem, has been signal generation upon binding of the target to the biosensor.

The present invention is directed to the development of a multi-target biosensor through the use of nucleic acid based, signal-generating ligands that can be used for detecting analytes. The signal-generating ligands of the present invention are derived from oligonucleotides (single-stranded RNA, DNA or modified variants of these structures). These oligonucleotides are refer to as aptamers. Aptamers are used as the basis for the signal-generating ligands because they have the capacity for forming a virtually limitless array of shapes, sizes and configurations and thus are capable of forming specific binding pairs with virtually any chemical compound, whether monomeric or polymeric. A procedure for the selection of aptamers that bind a desired target has been disclosed in U.S. Pat. No. 5,843,653, and is named SELEX. However, this method does not provide for a signal-generating ligand. Advantageously, the present invention provides a ligand complex with enhanced target selectivity as well as a means for the complex to produce a detectable signal upon binding to its specific target analyte.

The present invention uses two aptamers that recognize different epitopes of the same target molecule. The two aptamers are coupled together to create a new structure, termed a biaptamer. The construction of the biaptamer is based on the inventors' insight that the coupling together of two aptamers dramatically increases the affinity and selectivity of the ligand complex (biaptamer) for the target analyte, because binding becomes cooperative. Furthermore, this enhanced specificity and affinity for the target analyte reduces the need to exhaustively select for highly specific, high affinity aptamers for each target. In addition, a biaptamer will undergo a conformational change when it binds to the target analyte. The conformational change is a change in the separation and/or the angle between the two aptamer components of the biaptamer. This change is exploited in the present invention to create a signal-generating mechanism. The biaptamer is altered by the addition of fluorophores (defined here as fluorescent or luminescent entities, or chromophores). Interaction of the target analyte with this modified biaptamer changes the characteristics of the photon absorption or emission from the modified biaptamer. These changes provide a real time detection of the binding event. The prior art has failed to teach or suggest the fusion of multiple aptamers to create biaptamers with intrinsic signaling properties.

Several properties of the photon absorption or emission of paired fluorophores change with changes in their spatial arrangement. For example, if two fluorophores are used that possess a substantial overlap between the emission spectrum of one of the pair (the donor) and the excitation spectrum of the other (the acceptor), then the excitation of the donor can result in transfer of energy to the acceptor. This process is termed resonance energy transfer (RET). RET is very sensitive to the distance and angle between the fluorophores. It can be detected as a decrease in donor emission or fluorescence lifetime, or by an increase in acceptor emission or lifetime. Conformational changes can also lead to changes in the anisotropy properties of the fluorophores.

In accordance with one embodiment of the invention the signal-generating ligands of the present invention are bound to a solid surface. In this embodiment, fluorescence energy transfer in combination with established DNA chip technology allows the system to be easily multiplexed.

SUMMARY OF THE INVENTION

The present invention provides oligonucleotide-based biosensors and a general method for their production and use. Specifically, the invention describes a novel use for oligonucleotide aptamers that have been selected against target molecules of interest. The invention describes the combination of these aptamers into "biaptamers" that show co-operative binding to the target, and which have an enhanced probability of undergoing a conformational change on binding to the target molecule. The biaptamers are further provided with a signaling system that provides a detectable signal upon binding of the biaptamer to its specific analyte. Energy transfer is induced by the conformational change in the biaptamer caused by the interaction of its two distinct binding sites with the target.

DETAILED DESCRIPTION OF THE INVENTION

In describing and claiming the invention, the following terminology will be used in accordance with the definitions set forth below.

As used herein, "nucleic acid," and "oligonucleotide" encompass single and double-stranded RNA and single and double-stranded DNA and cDNA. "Nucleic acid," "oligonucleotide," and similar terms also include nucleic acid analogs, i.e. analogs having other than a phosphodiester backbone, or that contain modified bases. For example, the so-called "peptide nucleic acids," which are known in the art and have peptide bonds instead of phosphodiester bonds in the backbone, (Nielsen et al. Science 254, 1497 (1991)), are considered within the scope of the present invention.

As used herein, the tern "aptamer" encompasses an oligonucleotide that interacts with a target analyte. Generally, aptamers have been selected from a large number of non-interacting oligonucleotides.

As used herein the term "fluorophore" will be understood to refer to both fluorophores, phosphors and luminophores, and to chromophores that absorb but do not emit photons.

As used herein RET is intended to include the situation where the acceptor fluorophore absorbs photons from the donor fluorophore and emits the energy as fluorescence as well as the situation where the acceptor fluorophore is a quencher that absorbs photons from the donor fluorophore without a corresponding emission of photons.

As used herein, the term "purified" means that the molecule or compound is substantially free of contaminants normally associated with the molecule or compound in a native or natural environment.

As used herein the term "non-complementary nucleic acid sequences" will be understood to refer to nucleic acid sequences that are not capable of precise pairing (of purine or pyrimidine bases between the two strands of nucleic acids sequences) under moderate or stringent hybridization conditions (i.e. 5–10° C. below Tm). "Complementary nucleic acid sequences" are two sequences that will form a duplex (precise pairing of purine or pyrimidine bases) under moderate or stringent hybridization conditions.

The present invention is directed to novel signal-generating ligands of the general formula:

$F_1$-A-L-B-$F_2$ wherein $F_1$ and $F_2$ represent components of a signaling system that generates a distinct detectable signal upon binding of the complex with the target analyte. A and B represent ligands that independently bind to a target analyte and L is a linking moiety. The general structure A-L-B is referred to herein as "biaptamer".

In accordance with one embodiment, the signaling system used in accordance with the present invention comprises one or more fluorescent entities linked to the signal-generating ligand. Binding of the analyte to the signal-generating ligand quenches the fluorescence of the fluorophore(s) or otherwise alters the absorption or emission characteristics of the fluorophore(s). Such changes can be detected and correlated qualitatively or quantitatively with the presence of analyte binding. In one embodiment fluorescent resonance energy transfer (FRET) is used to detect the binding of the analyte to the signal-generating ligand. In this embodiment a pair of fluorescent moieties (fluorophores) and/or luminescent or phosphorescent moieties (luminophores) are attached to the ends (or close to the ends) of the two ligands (A and B in the general formula $F_1$-A-L-B-$F_2$) of the signal-generating ligand complex. When the signal-generating ligand binds to the target analyte, the distance and/or angle between the fluorophore pairs will be changed. This change can be detected because it will change the efficiency of resonance energy transfer between the moieties after exposure of the signal-generating ligand complex to an excitation wavelength of light.

The efficiency of resonance energy transfer varies with the sixth power of the separation between the donor and acceptor fluorophores, and therefore provides a very sensitive readout of changes in the separation caused by target binding. In one preferred embodiment, $F_1$ and $F_2$ of the general formula $F_1$-A-L-B-$F_2$ represent an acceptor fluorophore and a donor fluorophore, respectively, wherein the donor fluorophore has an emission spectrum that overlaps with the absorption spectrum of the acceptor fluorophore.

The signal-generating ligand complex also comprises two binding ligands (A and B in the general formula $F_1$-A-L-B-$F_2$) that specifically bind to two different regions of the target analyte species. The binding ligands can be selected from antibodies, receptors, nucleic acids or other compounds capable of specific binding to target analyte species. In accordance with one preferred embodiment the binding ligand comprises RNA or DNA oligonucleotides that have the capability of recognizing and binding to specific molecular targets with high affinity and selectivity. Such oligonucleotides are referred to as aptamers. The preparation of aptamers has been previously described in Tuerk C, Gold, L Science 249:505–510 (1990); Klug S J, Famulok M Mol Biol Reports 20:97–107 (1994); and Morris K N et al, Proc. Natl. Acad. Sci. USA 95:2902–2907 (1998) and in U.S. Pat. Nos. 5,843,701 and 5,843,653 the disclosures of which are expressly incorporated herein by reference.

In general, the procedure for preparing aptamers against specific targets requires as a first step, the preparation of a library of oligonucleotides. This library can be synthesized using combinatorial chemistry techniques that are known to those of ordinary skill in the art. In accordance with one embodiment, a random library of oligonucleotide 30-mers (containing about $10^{18}$ different sequences) is prepared. The library size can be increased by making longer nucleotide strands (i.e. oligonucleotides ranging in size from about 30 to about 60 nucleotides in length) or by including chemically modified bases. Each end of the random sequence is flanked by 10 further bases that are of a constant, known sequence. The oligonucleotide library is then screened by affinity chromatography, and in one embodiment the screening process is multiplexed.

In accordance with one embodiment the affinity column used to screen the oligonucleotide library comprises a diverse array of biological material isolated from a particular individual, organism or material sample (i.e. a soil, air or water sample). Biological material, including but not limited to proteins, carbohydrates, nucleic acids, lipids, glycoproteins can be bound to a solid surface using standard techniques known to those skilled in the art. The solid surface can be selected from any surface that has been used to immobilize biological compounds and includes but is not limited to polystyrene, agarose, silica or nitrocellulose. In one embodiment the solid surface comprises functionalized silica or agarose beads.

In accordance with one embodiment the components of a sample are bound to silica or agarose beads in separate reactions using different reaction conditions to ensure that a diverse array of compounds are bound to the solid surface. Fractions of these separate reactions can then be combined to form a single affinity chromatography column.

The mixed target affinity chromatography column is then incubated with one or more components of the oligonucleotide library. Oligonucleotides that interact nonspecifically to the matrix are removed prior to screening using standard techniques. For example, in accordance with one embodiment the oligonucleotide library can be contacted with an affinity column that lacks any compounds from the target biological sample. Alternatively, the oligonucleotide library can be first be contacted with compounds that are known to bind non-specifically with oligonucleotides under the preselected experimental conditions.

After incubation to allow binding of the oligonucleotide library components, the mixture is stringently washed to remove unbound oligonucleotides. Oligonucleotides that bind to the targets are then eluted by washing the bound oligonucleotides with a buffered solution, under increased ionic strength or under increased temperatures or a combination thereof, using standard techniques known to those skilled in the art. In accordance with one embodiment the bound oligonucleotides are eluted by washing the mixtures at increased temperatures ranging from about 80° C. to about 100° C. and more preferably at about 95° C.

Specifically eluted oligonucleotides are amplified by the polymerase chain reaction (PCR) using primers that bind to the flanking sequences. PCR is an exemplary method for amplifying of nucleic acids (See U.S. Pat. Nos. 4,683,195, and 4,683,202). The PCR will be carried out under mutagenic conditions by an established method so as to increase the complexity of the products (See Zhou, Y. H. et al. R. H. Nucleic Acids Res. 19: 6052 (1991)). RNA aptamers are converted to cDNA by reverse transcriptase using standard techniques prior to conducting the PCR reaction. The products are converted back into RNA, if desired, using an RNA polymerase. This mutagenesis procedure enhances the affinity of molecules in the starting pool that have an initial low affinity for the target, and thus generates higher affinity receptors in subsequent generations. DNA aptamers are isolated from the PCR products by separation of the two DNA strands, using standard methods known to those skilled in the art. After several iterations, the oligonucleotides that are specifically retained on the column are sequenced. These selected oligonucleotides are referred to as aptamers. Typically, sequencing oligonucleotides obtained after 5–10 rounds of selection reveals that the selected products are homologs (based on their primary sequences and secondary structure). This characteristic indicates that selection is near completion.

The isolated aptamers can be tested individually for their ability to bind to each of the target components. In particular, the isolated aptamer can be bound to a solid surface and screened with the original sample to identify the compound or compounds present in the sample that specifically bind to the aptamer.

The aptamers will also be synthesized without the constant known region at each end. The affinity for the targets of the aptamers, with or without the constant known region, can be determined directly by performing a binding assay. In this assay the aptamers are first labeled with a detectable marker, for example, radiolabeled using $^{32}$P-$\gamma$ ATP of known specific activity and T4 polynucleotide kinase. The immobilized target is incubated with the radiolabeled aptamer. After allowing time for binding the target is washed and the amount of bound labeled aptamer is determined by scintillation counting. From a plot of the amount of bound aptamer versus the free concentration of aptamer the binding affinity of the aptamer for the target can be determined. If the constant known region does not enhance the binding affinity for the target it will not be included in the subsequent steps.

To further enhance the ability of the aptamers to bind and identify specific target analytes, two aptamers that show mutually independent binding to a specific target are linked together to form a "biaptamer". The purpose of linking two aptamers together is two-fold. First, it enhances the binding affinity of the oligonucleotide for the target by creating a molecule that undergoes co-operative binding with the target. Second, it increases the probability that the oligonucleotide will undergo a large conformational change on binding the target.

The aptamers are bound to one another through a linker (L) moiety. Typically the aptamers will be covalently bound to the linker, however other linking associations, including ionic and hydrogen binding, are also possible. The linker can be any suitable polymer that provides a flexible polymeric backbone and does not interfere with the ability of the two aptamers to independently bind to the target analyte. Such polymeric linkers are known to those skilled in the art and include but are not limited to polypeptides, polyamines, nucleic acids, polyethylene glycol and other synthetic structures. The purpose of the linker is to optimize the distance between the donor and acceptor fluorophores and thereby enhance the signal-to-noise ratio on target binding. The optimal length of the linker will be determined empirically and may vary from biaptamer to biaptamer, and with target structure.

In accordance with one embodiment when the linker comprises a polymer other than DNA or RNA (for example polyamines, polypeptides or other synthetic structures), multiple aptamers can be linked to the polymer backbone of the linker to form a "polyaptamer." The number, density and diversity of the aptamers can be varied to adjust the selectivity and affinity of the signal-generating ligand complex. For example three or more different aptamers that bind to unique targets can be linked to a single linker polymer. The relative ratio of the different aptamers can be varied, as well as the density of the aptamers on the linker, to obtain the desirable binding characteristics. Fluorophores can be linked to the polymer linker such that binding of an analyte to the signal-generating ligand complex alters the conformation of the signal-generating ligand complex and produces a detectable signal.

Creation of Biaptamers

In order to construct a biaptamer it is necessary to identify at least two different aptamers (A and B) that show mutually independent binding to a specific target, and which are not complementary sequences. One standard method to screen for aptamers that bind different epitopes is based on competition assays. In one format of the competition assay, one of the aptamers (A) is labeled with a detectable marker, for example by radiolabeling the aptamer, and used in a binding assay with the target. Increasing concentrations of the other unlabeled aptamer (B) are also added. If the unlabeled aptamer B does not decrease the amount of labeled aptamer A that binds to the target then the aptamers have mutually independent binding to the target. Other possible methods include determination of the binding sites on the target by X-ray crystallography or by other structural studies, or by altering discrete regions of the target surface, for example by mutagenesis.

The sequences of nucleotides that constitute each aptamer A and B are determined by DNA or RNA sequencing. A typical length for each aptamer is 30 bases, however the length of the aptamer can range from about 10 to about 100 bases, more preferably about 20 to about 50 bases. The distance between the distinct binding sites will be varied by incorporating linker regions of varying lengths of nucleotide bases between the sites. The length of this linker ranges from 0 to about 50 or more bases. The optimum length will be determined empirically. In accordance with one embodiment the linker comprises a nucleic acid sequence that is covalently linked to aptamer A at one end and aptamer B at the other end. In accordance with this embodiment the aptamers and the linker portion of the signal-generating ligand complex of the present invention can be synthesized as a single oligonucleotide that consists of aptamer A sequence, followed by a linker sequence, followed by aptamer B sequence.

In accordance with one embodiment of the present invention the linker comprises a nucleic acid sequence that includes a segment complementary to a separate, short "tuning oligonucleotide." The purpose of the tuning oligonucleotide is to further enhance the signal-to-noise ratio upon target binding to the signal-generating ligand complex. The principle of action of the tuning oligonucleotide is to bind to the linker and form a rigid duplex helix between the two aptamers that form the biaptamer. This helix will hold the target binding sites apart, and maintain a distance between the donor and acceptor fluorophores such that the efficiency of resonance energy transfer between them is very low (<20%) in the absence of target analyte binding to the signal-generating ligand complex. In one preferred embodiment the tuning oligonucleotide is designed so that the duplex formed between the tuning oligonucleotide and the linker sequence has a low melting temperature, to ensure that the tuning oligonucleotide is displaced upon binding of the target analyte. The necessity for the tuning oligonucleotide is determined empirically.

The criteria for determining the optimum length of the biaptamer linker and for determining the necessity for inclusion of a tuning oligonucleotide (or for determining the aptamer density in the polyaptamer) include the effect on the affinity for the target (as described above), and the magnitude of the change in the efficiency of the fluorescence resonance energy transfer (FRET), luminescence resonance energy transfer (LRET) or other changes in the donor and/or acceptor fluorophore excitation and emission characteristics, after binding of the signal-generating ligand complex with its specific analyte.

Signal Generation

The biaptamer is further provided with a signaling system such that a detectable signal is generated upon target molecule binding. In one embodiment of the invention, paired donor/acceptor fluorophores are covalently linked to or incorporated into the ends (or near the ends) of the biaptamer. Pairs are chosen such that there is substantial overlap between the emission spectrum of the donor fluorophore (D) and the excitation spectrum of the acceptor fluorophore (A). Under conditions where the separation of A and D is less than about 80 Angstroms, excitation of fluorophore D can cause fluorescence resonance energy transfer (FRET) to A, which will then emit light (Clegg, R M, Curr Opinion Biotech 6:103–110 (1995)).

The signal-generating ligand complexes are designed such that initially the distance between the acceptor and donor is too great to allow efficient transfer of energy from the donor to the acceptor in the absence of the target analyte. Target analyte binding alters the separation between the paired fluorophores on the biaptamer, which changes the efficiency of resonance energy transfer between them. The efficiency of transfer varies with the 6th power of the distance between the acceptor and the donor fluorophores, and also varies with the orientation of the transition dipoles of the donor and acceptor fluorophores. FRET is therefore very sensitive to small changes in proximity. The typical length of the extended biaptamer (~100 bases) is calculated to be 200 Å. Even with folding due to secondary structure formation, the unliganded aptamer is likely to be sufficiently long to keep FRET to a minimum. However, interaction of the target with the two distinct binding sites on the biaptamer will induce a substantial change in the conformation of the biaptamer, which will reduce the separation between the fluorophores, and thereby increase the FRET signal.

In one embodiment, the biaptamer is synthesized with a 5' sulfhydryl group and a 3'-amino group. An amino group-reactive fluorophore, such as fluorescein-succinimydyl ester, is reacted with the 3' end of the biaptamer. Then the trytyl moiety, which protects the 5' end, is removed with silver nitrate, and the biaptamer is reacted with an appropriate sulfhydryl-directed reagent, such as tetramethylrhodamine iodoacetamide. The biaptatner is purified by high pressure liquid chromatography.

In another embodiment of the present invention, additional oligonucleotide sequences are attached to each end of the signal-generating ligand, to produce a structure of the general formula:

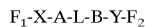

$F_1$-X-A-L-B-Y-$F_2$ wherein $F_1$ and $F_2$ represent components of a signaling system that generates a distinct detectable signal upon binding of the complex with the target analyte. A and B represent aptamers that independently bind to a target analyte, wherein A and B specifically bind to a non-nucleic acid epitope. In accordance with one embodiment, A and B bind to a specific peptide epitope. L is a linking moiety and X and Y are short, complementary oligonucleotide sequences. A preferred length of X and Y is about 3 to about 15 nucleotides and more preferably about 5 to about 7 nucleotides, such that the melting temperature is less than 50° C. Furthermore, X and Y are designed to hold $F_1$ and $F_2$ in close proximity in the absence of a target analyte. Binding of the target to the biaptamer region of the biaptamer component (A-L-B) of the complex forces the separation of X and Y, and increases the distance between $F_1$ and $F_2$. This change in distance is detected as a change in the emission and/or excitation characteristics of the $F_1$ and/or $F_2$ fluorophores. In one embodiment, one of the two fluorophores is DABCYL(4(4'-dimethyl amino phenylazo)benzoic acid).

As another specific example of the present invention, commercially available fluorescein-12-dUTP is incorporated during synthesis near or at the 5' end of the biaptamer, using a standard automated synthesis protocol. Carboxytetramethylrhodamine (CTMR)-12-dUTP is also incorporated during synthesis near or at the 3' end of the biaptamer. The overlap between the fluorescein emission and the CTMR excitation spectra is such that resonance energy transfer can occur with an efficiency of 50% (the Förster radius) when the two fluorophores are separated by a distance of about 55 Ångstroms (Van der Meer, B. W. et al. Resonance Energy Transfer Theory and Data. VCH Publishers (1994)). Binding of target to the modified biaptamer will cause a conformational change in the biaptamer that will alter the distance between the fluorophores and therefore alter the FRET efficiency. The change in efficiency can be detected as an increase in the emission amplitude from the CTMR acceptor fluorophore, an increase in the lifetime of the CTMR, a decrease in the emission amplitude of the fluorescein donor fluorophore, or a decrease in the lifetime of the fluorescein. In a different embodiment of the method, changes in the anisotropy of the fluorophores are measured.

In another embodiment of the present invention, other fluorophore pairs are incorporated, such as (but not limited to) Cascade Blue/fluorescein, and Oregon Green/Carboxyrhodamine. For example, a luminescent donor is incorporated at or near one end of the aptamer, and a suitable fluorescent acceptor is incorporated at or near the other end. In a specific example, the luminescent donor is a lanthanide chelate such as europium or terbium DTPA-cs124 (diethylenetriaminepentacetate-carbostyril 124), and the acceptor is CTMR or Cy5 (Selvin, P. R. and Li, M. J. Am.Chem. Soc. 117: 8132–8138 (1995)). The Förster radius for a terbium DTPA-cs124/CTMR pair is about 60 Angstroms (Getz, E. B. et al. Biophys. J. 74; 2451–2458 (1998)). In another embodiment, the acceptor is a chromophore that functions as a quencher of donor emission. One example of such a quencher is DABCYL (4(4'-dimethyl amino phenylazo)benzoic acid).

Optimally, the change in the separation between the donor and acceptor fluorophores caused by binding of the target molecule to the biaptamer will be sufficient to change the energy transfer efficiency by >25%. To optimize the change in FRET efficiency induced by target binding, the length of the linker section, and the inclusion of a tuning oligonucleotide are assessed, using biaptamers that contain the same aptamer sequences but which are separated by different linker sequence lengths. In addition, in one embodiment small oligonucleotides that are of different lengths and are complementary to a part of the linker sequence are synthesized, to act as tuning oligonucleotides. Alternatively, if polymers other than nucleic acids are used as the linker, the density of coupling of the aptamers to the polymer can be changed to identify the optimal change in FRET efficiency upon target analyte binding. FRET efficiency is then measured in the presence and absence of target, for the biaptamers with different linkers and/or with the addition of different tuning oligonucleotides. This procedure permits adjustment of the biaptamers to obtain a robust signal-noise ratio on binding of target.

The present invention also encompasses a biosensor comprising a solid matrix and a signal-generating ligand complex of the present invention wherein the signal-generating ligand complex is covalently linked to said solid matrix. Energy transfer between the fluorophores of the signal-generating ligand complexes is induced by the conformational change in the biaptamer caused by the interaction of its two distinct binding sites with the target. The biosensors are designed to detect a wide variety of target molecules, such as small organic molecules (eg., pesticides, herbicides, drugs, controlled substances, metabolites, explosive residues, plasticizers, industrial and agricultural pollutants, hormones), peptides and proteins (eg., surface antigens on viruses, peptide hormones, cellular components), polysaccharides (eg., surface antigens on bacteria and other pathogens), and other molecules.

In accordance with one embodiment the modified biaptamers are attached in a patterned array on a solid surface to create a multiplex biosensor chip, using established techniques, for example as described in: Ramsay, G. Nature Biotechnol 6:40–44(1998), Rogers. Y. H, et al. Anal Biochem 266:23–30 (1999), Lipshutz, R. J. Nature Genetics 21:20–24(1999). Binding of analyte targets by the modified biaptamers will change the fluorescence emission pattern produced by the chip, which will be detected by a CCD camera and laser, coupled with the necessary filters. In addition, fluorescence energy transfer combined with established DNA chip technology allows the detection system to be easily multiplexed.

In accordance with one embodiment the position of the emitting detection complex on the solid matrix is determined and used to identify the specific analyte(s) present in the sample. Advantageously, the detection complexes may not need to be specific to only one analyte, but rather a combination of detection complexes can be used to identify the presence of an analyte in a sample. Thus numerous biaptamers can be used to identify a single target and the biaptamers do not need to be perfectly specific. Thousands of biaptamers can be attached to a single chip and 10 or 20 different biaptamers can be used to detect a single target. This degeneracy reduces the chance of false positive signals and the need for absolute specificity, and increases the attainable degree of discrimination. In other words confirmation of the presence of an analyte may require a signal to be generated from two or more detection complexes identified by their location on the solid matrix.

The method of screening a sample for the presence of one or more analyte comprises the following steps. Firstly the signal-generating ligand complexes are contacted with the sample under conditions conducive for binding of the analyte to the signal-generating ligand complexes. The mixture containing the signal-generating ligand complexes and the sample is then exposed to a light source having a wavelength that is absorbed by the donor fluorophore but does not significantly overlap with the absorption spectrum of the acceptor fluorophore. The fluorescence from the mixture is then detected. In accordance with one embodiment the signal-generating ligand complexes are linked to a solid surface in a defined pattern to form a biosensor. The biosensor is then contacted with the sample for a predetermined length of time under conditions conducive for binding of the analyte to the signal-generating ligand complexes. The device is then exposed to a light source having a wavelength that is absorbed by the donor fluorophore but does not significantly overlap with the absorption spectrum of the acceptor fluorophore, and fluorescence from the biosensor is then detected.

In accordance with one embodiment the amount of fluorescence emitted from the fluorophore acceptor is detected. In particular, the signal is detected by a photodetector that is capable of distinguishing fluorescence emitted by the acceptor fluorophore from that emitted form the donor fluorophore. Thus the amount of analyte present is proportional to the amount of signal emitted by the acceptor fluorophore. In a preferred embodiment the photodetector is also capable of determining the location of the signal emitted relative to the position of each of the signal-generating ligand complexes present on the solid surface. In one embodiment a laser is used as the excitation light source and the emitted signals are detected by a CCD camera.

Alternatively, the step of detecting the analyte can be determined by the amount of signal emitted by the donor fluorophore, wherein the presence of analyte causes quenching of the donor fluorescence. For example, the acceptor fluorophore can be a chromophore that quenches the fluorescence or luminescence of the donor fluorophore when the donor and acceptor fluorophores are in close proximity. In this embodiment, binding of the analyte to the signal-generating complex changes the conformation of the signal-generating complex and brings the donor and acceptor fluorophores into close proximity and thus quenches the fluorescence or luminescence of the donor fluorophore.

Fluorescence energy transfer permits the real time detection of the binding event, and based on the intensity of the fluorescent signal, the FRET based signaling system can also be used to quantitate the amount of target analyte present in the sample. The signal-generating ligand complexes of the present invention are designed to operate in aqueous solutions, or in an aqueous film if they are attached to a solid matrix, within a temperature range of about 4° C. to about 40° C.

In accordance with one embodiment the biosensor device of the present invention (comprising a plurality of signal-generating ligand complexes linked to a solid surface) can be coated or enclosed within a semipermeable membrane or screen that excludes contact of the signal-generating ligand complexes with cellular debris and other large macromolecular material present in a sample. In accordance with one embodiment the semi-permeable membrane excludes particulate matter having a molecular weight greater than $1\times10^6$ daltons.

In one embodiment of the present invention the signal-generating ligand complex comprises a biaptamer composed of a single-stranded oligonucleotide (ribo- or deoxyribonucleotides) that may contain modified bases. Each aptamer is selected so as to bind to a different epitope on the same target molecule, which the biosensor is designed to detect. Donor and acceptor pairs of fluorophores are incorporated as modified nucleotides at or near the ends of the biaptamer. Furthermore, in one embodiment, the 5' and 3' ends of the biaptamer further include "constant sequences" that are required during initial selection of the aptamers. However, these constant sequences can be removed from the aptamers if assays determine they do not participate in the binding of the ligand to the analyte. The pairs of fluorophores are selected such that the Forster radius is about 50 Ångstroms.

The linker sequence is of variable length, selected empirically so that the average distance between the donor and acceptor, in the absence of target, is greater than about 80 Ångstroms, so that energy transfer is minimal. The signal-generating ligand complex also includes a tuning oligonucleotide in accordance with one embodiment. The tuning oligonucleotide is a short oligonucleotide complementary to a portion of the linker, such that it can form a duplex when annealed to the biaptamer. It is designed to have a low melting temperature (below about 45° C.) such that it will be easily displaced on target binding. The tuning oligonucleotide can also be complementary to a part of aptamer A or B to provide a similar function of reducing the signal to noise ratio.

Thus in accordance with the present invention a compound for detecting an analyte is provided wherein the compound has the general formula: $F_1$-A-L-B-$F_2$. $F_1$ and $F_2$ of that formula represent an acceptor fluorophore and a donor fluorophore respectively, wherein the donor fluorophore has an emission spectrum that overlaps with the absorption spectrum of the acceptor fluorophore. A and B of that formula represent ligands that independently bind to said analyte; and L is a linking moiety that links the two fluorophores together. In a preferred embodiment A and B represent non-complementary nucleic acid sequences and L is a nucleic acid sequence that is covalently linked to A and B. The detecting complex can further include a tuning oligonucleotide, wherein the tuning oligonucleotide comprises a nucleic acid sequence complementary to L.

What is claimed is:

1. A compound for detecting a target analyte, said compound having the general formula:

$$F_1\text{-A-L-B-}F_2$$

wherein $F_1$ represents an acceptor fluorophore and $F_2$ represents a donor fluorophore, wherein the donor fluorophore has an emission spectrum that overlaps with the absorption spectrum of the acceptor fluorophore;

A and B are aptamers comprising nucleic acid sequences that are non-complementary to each other, wherein A and B bind to different sites on said target analyte; and L is a linking moiety.

2. The compound of claim 1 wherein L is a nucleic acid sequence that is covalently linked to A and B.

3. The compound of claim 2 further comprising a tuning oligonucleotide, said tuning oligonucleotide comprising a nucleic acid sequence complementary to L.

4. A device for binding a target analyte, said device comprising
a solid matrix; and
a signal-generating complex covalently linked to said solid matrix, said signal-generating complex having the general formula:

$$F_1\text{-A-L-B-}F_2$$

wherein $F_1$ represents an acceptor fluorophore and $F_2$ represents a donor fluorophore, and the donor fluorophore has an emission spectrum that overlaps with the absorption spectrum of the acceptor fluorophore;

A and B aptamers comprising are nucleic acid sequences that are non-complementary to each other, wherein A and B bind to different sites on said target analyte; and L is a linking moiety.

5. The device of claim 4 wherein L is a nucleic acid sequence that is covalently linked to A and B.

6. The device of claim 5 further comprising a tuning oligo, said tuning oligo comprising a nucleic acid sequence complementary to L.

7. A compound for detecting a target analyte, said compound having the general formula:

$$F_1\text{-X-A-L-B-Y-}F_2$$

wherein $F_1$ represents an acceptor fluorophore and $F_2$ represents a donor fluorophore, wherein the donor fluorophore has an emission spectrum that overlaps with the absorption spectrum of the acceptor fluorophore;

A and B aptamers comprising are nucleic acid sequences that are non-complementary to each other, wherein A and B bind to different sites on said target analyte;

X and Y are nucleic acid sequences that are complementary to each other; and

L is a linking moiety.

8. The compound of claim 7 wherein X and Y are 5–7 nucleotides in length.

9. The compound of claim 7 wherein L is a nucleic acid sequence that is covalently linked to A and B.

10. The compound of claim 9 further comprising a tuning oligonucleotide said tuning oligonucleotide comprising a nucleic acid sequence complementary to L.

11. A device for binding a target analyte, said device comprising
a solid matrix; and
a signal-generating ligand complex covalently linked to said solid matrix, said signal-generating ligand complex having the general formula:

$$F_1\text{-X-A-L-B-Y-}F_2$$

wherein $F_1$ represents an acceptor fluorophore and $F_2$ represents a donor fluorophore, wherein the donor fluorophore has an emission spectrum that overlaps with the absorption spectrum of the acceptor fluorophore;

A and B aptamers comprising are nucleic acid sequences that are non-complementary to each other, wherein A and B bind to different sites on said target analyte;

X and Y are nucleic acid sequences that are complementary to each other; and

L is a linking moiety.

12. A method for detecting an analyte in a sample, said method comprising the steps of contacting one or more compounds of claim 1 with the sample to form a detection mixture;

exposing the detection mixture to a light source having a wavelength that is absorbed by the donor fluorophore but does not significantly overlap with the absorption spectrum of the acceptor fluorophore; and detecting fluorescence emitted from the detection mixture, wherein a detectable fluorescent signal is generated by the binding of the analyte to the compound of claim 1, and the detection of the signal indicates the presence of the analyte.

13. The method of claim 12 wherein the detection mixture comprises a plurality of said compounds having different analyte affinities.

14. The method of claim 13 wherein the compounds are linked to a solid surface.

15. The method of claim 14 wherein the step of detecting the fluorescence from the mixture further comprises the step of determining the position of a fluorescing compound on the solid surface.

* * * * *